(12) United States Patent
Linke et al.

(10) Patent No.: US 11,360,083 B2
(45) Date of Patent: Jun. 14, 2022

(54) OPTICAL MOLECULAR NANOWIRE SENSOR

(71) Applicants: Heiner Linke, Lund (SE); Alf Månsson, Kalmar (SE); Christelle Prinz, Lund (SE); Jonas Ohlsson, Malmö (SE); Cassandra Niman, San Diego, CA (US); Mercy Lard, Lund (SE); Aleksandra Dabkowska, Mö (SE); Nicklas Anttu, Lund (SE)

(72) Inventors: Heiner Linke, Lund (SE); Alf Månsson, Kalmar (SE); Christelle Prinz, Lund (SE); Jonas Ohlsson, Malmö (SE); Cassandra Niman, Lund (SE); Mercy Lard, Lund (SE); Aleksandra Dabkowska, Lund (SE); Nicklas Anttu, Lund (SE)

(73) Assignee: AlignedBio AB, Lund (SE)

( * ) Notice: Subject to any disclaimer, the term of this patent is extended or adjusted under 35 U.S.C. 154(b) by 636 days.

(21) Appl. No.: 15/327,971

(22) PCT Filed: Jul. 22, 2015

(86) PCT No.: PCT/EP2015/066772
§ 371 (c)(1),
(2) Date: Jan. 20, 2017

(87) PCT Pub. No.: WO2016/012504
PCT Pub. Date: Jan. 28, 2016

(65) Prior Publication Data
US 2017/0212106 A1    Jul. 27, 2017

(30) Foreign Application Priority Data
Jul. 22, 2014    (EP) ................................. 14178073

(51) Int. Cl.
*G01N 33/543*    (2006.01)
*G01N 21/64*    (2006.01)
(Continued)

(52) U.S. Cl.
CPC .. *G01N 33/54373* (2013.01); *B01L 3/502715* (2013.01); *B01L 3/502761* (2013.01);
(Continued)

(58) Field of Classification Search
CPC ....... G01N 33/54373; G01N 33/54366; G01N 21/6452; G01N 21/7703; G01N 21/645;
(Continued)

(56) References Cited

U.S. PATENT DOCUMENTS 5,671,303 A * 9/1997 Shieh ................. G01N 21/6454
356/128
2003/0198963 A1* 10/2003 Leonard ............... G01N 21/645
435/6.11
(Continued)

FOREIGN PATENT DOCUMENTS

| EP | 1804052 A1 | 7/2007 |
|---|---|---|
| WO | 2007092909 A2 | 8/2007 |
| WO | 2011014176 A1 | 2/2011 |

OTHER PUBLICATIONS

Shevgaonkar (Fiber Optics Lecture #7) Dept of Electrical Engineering, IIT Bombay (Year: 2020).*
(Continued)

*Primary Examiner* — Christopher L Chin
(74) *Attorney, Agent, or Firm* — The Marbury Law Group PLLC

(57) ABSTRACT

A nanowire molecular sensor, and a molecular detection system, comprising a nanowire waveguide (30), a nanowire sidewall (51) functionalized in order to attach a molecule (54), and light emissive point sources (52), wherein the
(Continued)

amount of light emitted at an end (53) of the waveguide is dependent of the amount of specific molecules attached to the sidewall of the nanowire. A method employing said sensor may be used for single cell detection and analysis.

19 Claims, 17 Drawing Sheets

(51) Int. Cl.
*G01N 21/77* (2006.01)
*B01L 3/00* (2006.01)
*G01N 33/542* (2006.01)
*B82Y 15/00* (2011.01)

(52) U.S. Cl.
CPC ....... *G01N 21/645* (2013.01); *G01N 21/6452* (2013.01); *G01N 21/7703* (2013.01); *G01N 33/542* (2013.01); *G01N 33/54366* (2013.01); *B01L 2300/0627* (2013.01); *B01L 2300/0858* (2013.01); *B01L 2300/0896* (2013.01); *B82Y 15/00* (2013.01); *G01N 2021/6441* (2013.01); *G01N 2021/6463* (2013.01); *G01N 2021/7786* (2013.01)

(58) Field of Classification Search
CPC ......... G01N 33/542; G01N 2021/7786; G01N 2021/6441; G01N 2021/6463; B01L 3/502715; B01L 3/502761; B01L 2300/0627; B01L 2300/0858; B01L 2300/0896; B82Y 15/00
USPC ........... 385/12; 422/82.08, 82.11; 435/288.7; 436/524, 805; 977/721, 762, 954, 958
See application file for complete search history.

(56) References Cited

U.S. PATENT DOCUMENTS

| | | | |
|---|---|---|---|
| 2005/0029464 A1* | 2/2005 | Babayoff | G02B 21/0056 250/370.08 |
| 2006/0159916 A1* | 7/2006 | Dubrow | B01J 20/3289 428/357 |
| 2006/0269927 A1 | 11/2006 | Lieber | |
| 2007/0070341 A1* | 3/2007 | Wang | G01J 3/44 356/301 |
| 2007/0196043 A1* | 8/2007 | Peled | G01N 21/774 385/12 |
| 2008/0149944 A1 | 6/2008 | Samuelson | |
| 2011/0189783 A1* | 8/2011 | Andrew | G02B 6/107 436/149 |
| 2011/0268610 A1* | 11/2011 | Recknor | G01N 21/45 422/63 |
| 2015/0024507 A1* | 1/2015 | Han | G01N 21/7746 436/149 |

OTHER PUBLICATIONS

International Search Report and written Opinion for PCT/US2015/066772, dated Jan. 28, 2016.
Office Communication from European Patent Office, Final Instructions and European Search Report for European Patent Application No. 14178073.4, dated Dec. 13, 2016, 8 pages.
Office Communication from European Patent Office, Communication Pursuant to Article 94(3) EPC and Annex to the Communication for European Patent Application No. 15741181.0, dated Jun. 6, 2018, 4 pages.
Office Communication from European Patent Office, Communication Pursuant to Article 94(3) EPC and Annex to the Communication for European Patent Application No. 15741181.0, dated Nov. 26, 2019, 4 pages.

* cited by examiner

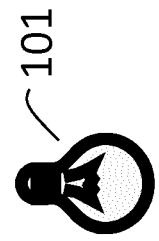
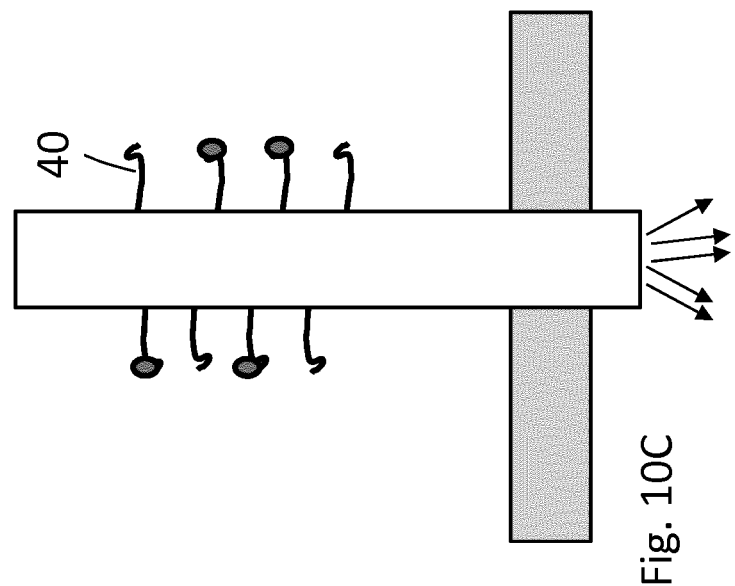
Fig. 10C
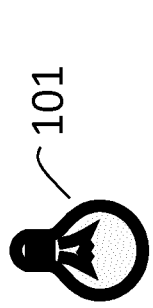
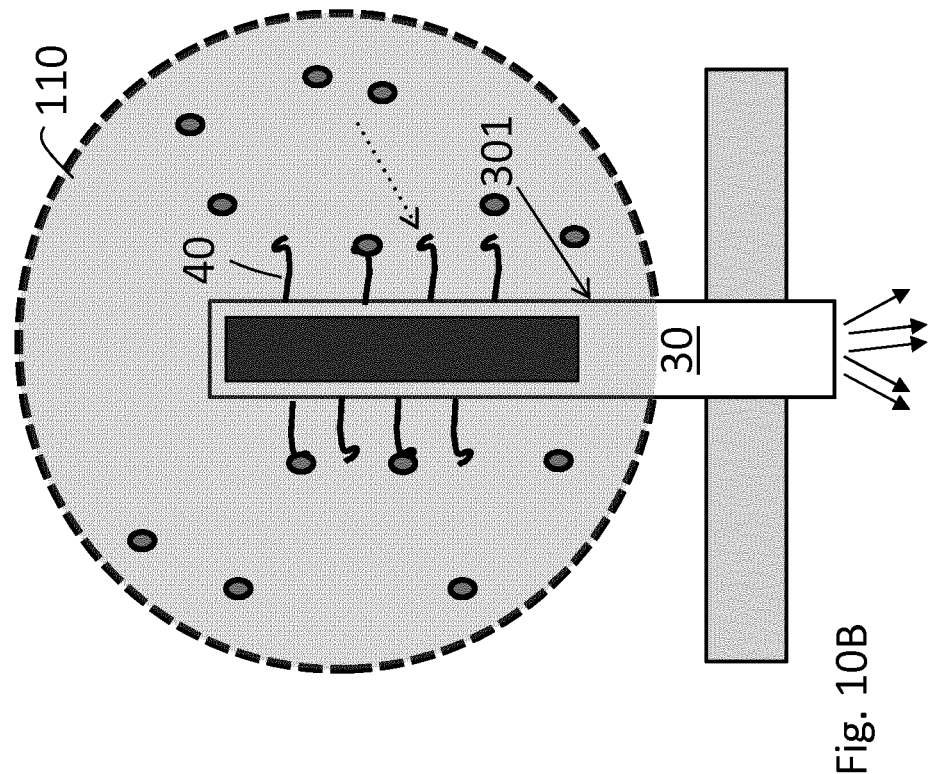
Fig. 10B

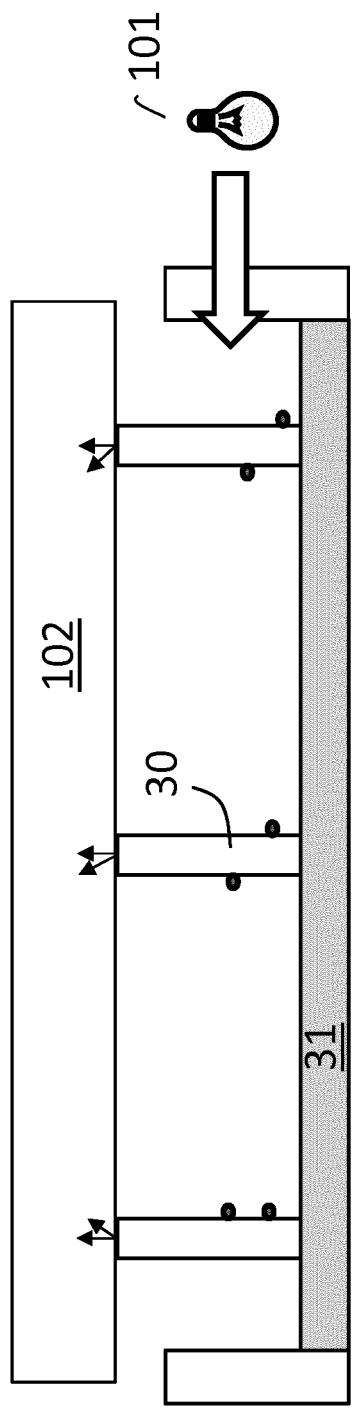
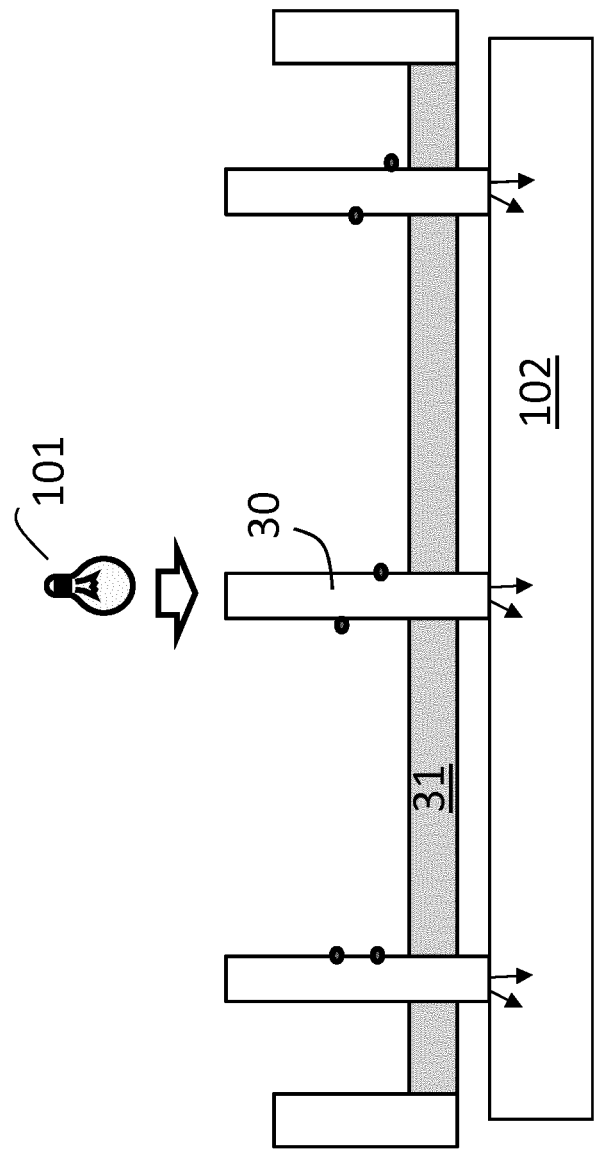

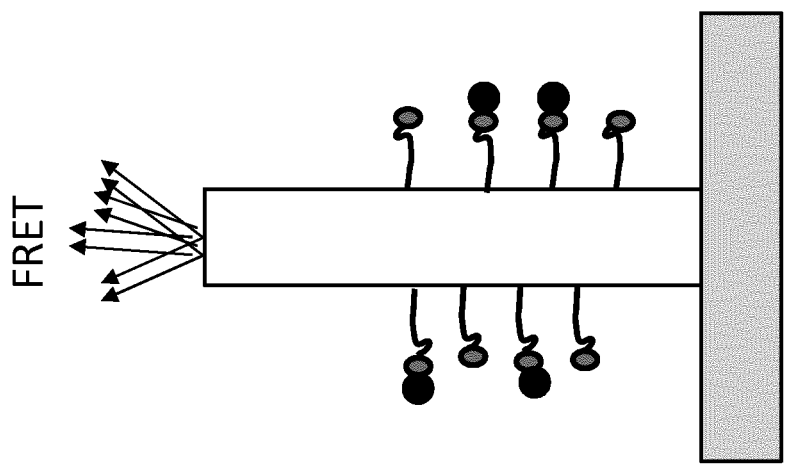
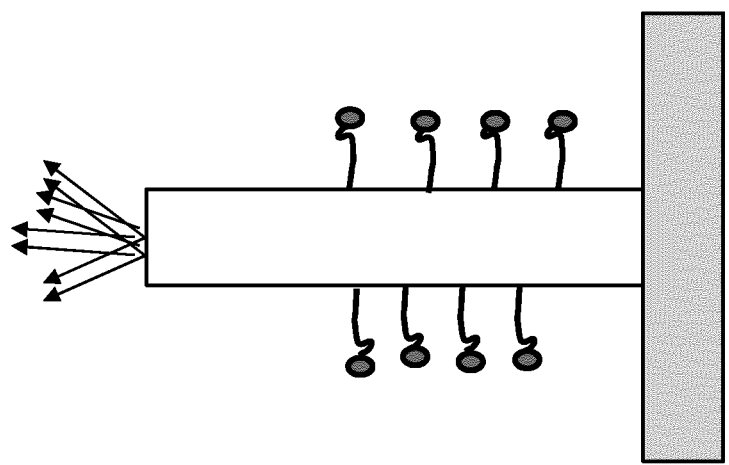
Fig. 12

OPTICAL MOLECULAR NANOWIRE SENSOR

CROSS-REFERENCE TO OTHER APPLICATIONS

This application is a national phase application under 35 U.S.C. § 371 of international application PCT/EP2015/066772, filed Jul. 22, 2015 which claims priority to European Application No. 14178073.4 filed on Jul. 22, 2014, the entire teachings of which are incorporated herein by reference.

FIELD OF THE INVENTION

The invention comprises a method and device to, through optical means, detect, analyze, and differentiate surface adhered molecules and atoms, such as biological molecules or elements from a bulk solution, in liquid or gas phase, with high sensitivity and localized readout.

BACKGROUND

In standard immunometric methods (Wild, 2013) recognition molecules such as antibodies or oligonucleotides are immobilized on solid supports in the form of flat surfaces, e.g. in microwell plates. Analyte capture by the immobilized recognition molecules is the basis for detecting the presence of analyte. This capture may be detected by specific binding of another set of recognition molecules which recognize another region of the analyte than the one mediating binding to the flat support. Often these secondary recognition molecules are labeled with fluorophores or enzymes where the latter catalyze the formation of a colored product. These methods are denoted fluorescence linked immunosorbent assays, so called FLISAs when fluorescence based detection is used and enzyme-linked immuno-sorbent assays so called ELISAs in the other case.

Conventional microarrays are conceptually similar to FLISAs. However, instead of surface immobilization of specific recognition molecules on the bottom surface of a microwell, spots of specific oligonucleotide-probes are printed (REF) on micrometer-sized areas with a given position for a given probe type. The oligonucleotide sample to be studied is subjected to a biotinylation process and then allowed to react with the oligonucleotide probes on the surface. This leads to specific binding reactions so that different oligonucleotides in the sample hybridize with exactly complementary nucleotide sequences on the surface. Subsequently, fluorescent streptavidin or similar specific biotin binding proteins are added causing accumulation of fluorescence on surface printed spots to which oligonucleotides in the sample have specifically hybridized. In this way, the degree of observed fluorescence intensity, in a specific spot, gives quantitative information about the amount of the oligonucleotide in the sample that is complementary to the oligonucleotide probe in that spot.

Another known detection technique is surface plasmon resonance (SPR; e.g. Biacore, GE Healthcare) which is routinely used in bioaffinity studies to monitor changes in the signal detected from the interface upon binding of a molecule from solution onto a surface. In this way, the extent to which a target molecule interacts with a binding partner immobilized on the surface can be measured in real time. Dual polarization inferometry (DPI; e.g. AnaLight®, Far-field) is used to obtain thickness and refractive index of a layer of adsorbed molecules within the evanescent wave.

In one existing approach, the TIRF (total-internal reflection fluorescence) technique is used, which employs a near-field effect to selectively excite only those molecules that are within a very short distance (typically on the order of 100 nm) from a surface and even though standard techniques for global detection are used only the excited molecules near the surface contribute to the emission signal. TIRF microscopy technique requires specific and complex optics for the optical excitement of fluorescent markers, which achieves spatial selectivity by using an optical near-field effect implemented through total internal reflection at the detection surface.

In existing microarrays, the detection sensitivity is limited by the density of immobile recognition molecules that can be achieved on a flat surface. In principle, the effective surface area could be increased significantly by introducing topological features with larger, effective surface area, but then, the optical read-out becomes a limiting factor because the recognition molecules then are located in different focal planes.

Furthermore, in existing optical sensing technology that uses detection of fluorescent markers, it is a challenge to distinguish target molecules or target particles that are selectively bound to a specific target area, from other fluorescent molecules or particles that are free in solution. This applies to the conventional method. The problem in this case is partly due to background fluorescence, including the presence of fluorescent antibody in the solution and non-specific binding of fluorescent antibody, i.e. without the target analyte present, to the sensor surface. The introduction of highly miniaturized sensors e.g. nanosensors, circumvents this problem due to the reduced surface area of the sensor. However, new problems are introduced by this approach because small detector areas severely compromise the rate of transport by diffusion (SheehanandWhitman, 2005) and reduce the output signal. Similar problems as in the FLISA methods apply in the case of microarrays described above. The present invention circumvents these problems by reducing sensor area laterally, while relying on high surface to volume ratio (i.e. into bulk solution) to improve rate of detection and signal to noise ratio.

The TIRF microscopy technique reduces problems with background fluorescence by utilizing local excitation (i.e. over a subset of the total sample volume) and global detection. The primary drawback is that TIRF requires precise alignment of a laser excitation source, which is difficult to incorporate in current commercial approaches due to extreme sensitivity to outside perturbation. Different from TIRF, our invention relies on global excitation (i.e. over a larger sample volume). Similar to TIRF, we can use global detection (in the focal plane), while still relying on high signal-to-noise ratio at detector sites due to near-field signal enrichment. As will be shown, the present invention circumvents the main problem in TIRF microscopy, by being easily integrated into current commercial platforms without the need for carefully aligned laser source excitation.

SUMMARY OF THE INVENTION

Contrary to standard TIRF technology, the invention comprises a molecular sensor including nanowires for optical wave-guiding. More specifically, embodiments of the invention relate to a device and a method to precisely monitor the selection of specific molecules at a surface through light emission from one focal plane. In one application it relates to a molecular sensor for detection of concentration and/or presence of specific molecules in a gas or liquid solution.

In accordance with one distinguishing feature of the invention, the sensor is configured to only allow light emitted in absolute proximity of a nanowire side-surface to be coupled into the nanowires, due to a near field (NF) or fluorescence resonant energy transfer (FRET) coupling mechanism between point light sources and the nanowire waveguide. Light coupled into the nanowire is subsequently connected to a detector. Light coupling may be obtained from molecules acting as surface attached light emissive point sources (SALEPS).

The invention is defined in the claims, and specific details and embodiments are outlined within the detailed description and drawings.

According to a first aspect, the invention relates to a nanowire molecular sensor comprising a nanowire projecting from a front side of a substrate, the nanowire having two ends and a sidewall, which sidewall is functionalized in order to attach a molecule, wherein the nanowire is a waveguide configured to receive light from light emissive point sources at the sidewall and to emit light from an end of the nanowire, wherein the amount of light emitted is dependent on the amount of specific molecules attached to the sidewall.

In one embodiment, the nanowire molecular sensor is configured such that a specific molecule may replace or release a light emissive point source from the sidewall, so as to decrease the light emitted from the end of the nanowire.

In one embodiment, the nanowire molecular sensor is configured such that a specific molecule may un-quench a light emissive point source at the sidewall, so as to increase the light emitted from the end of the nanowire.

In one embodiment, the nanowire molecular sensor is configured to emit light at the end of the nanowire waveguide which comprises light that is coupled in from surface attached light emissive point sources at the sidewalls.

In one embodiment, the nanowire is configured to receive light from light emissive point sources by means of a near-field coupling mechanism.

In one embodiment, said nanowire projects away from the front side of the substrate to a first nanowire end, and is attached to the substrate adjacent to a second nanowire end.

In one embodiment, the light emissive point sources are attached to the specific molecules.

In one embodiment, the light emissive point sources are attached to the functionalized nanowire sidewall.

In one embodiment, one end of the nanowire is optically connectable to an excitation device for injecting light into the nanowire, such that light is guided through the nanowire waveguide to excite the light emitting point sources.

In one embodiment, light guided through the nanowire is configured to excite surface attached light emitting point sources indirectly via FRET.

In one embodiment, excitation is light coupled into the nanowire through the second end at a rear side of the substrate.

In one embodiment, light is emitted from the nanowire waveguide through said second end.

In one embodiment, light is emitted from the nanowire waveguide through said first end.

In one embodiment, the light emissive point sources comprise fluorophores.

In one embodiment, the nanowire has internal properties is tuned to its surface chemistry to optimize light collection at a distance of less than half the wavelength of fluorescent light from the nanowire sidewalls, and where the fluorescence of fluorophores that are directly adsorbed to the nanowire sidewalls is either suppressed or quantified for later subtraction.

In one embodiment, the nanowire is configured such that a light from a light emissive point source at said sidewall can be coupled directly to a wave-guiding mode in the nanowire.

In one embodiment, the nanowire waveguide comprises an end point member at the first end, which end point member is configured so as to couple light between the nanowire and a region exterior to the sidewall.

In one embodiment, a plurality of nanowires with functionalized sidewalls are arranged mutually spaced apart to project substantially parallel to each other from said substrate.

In one embodiment, the nanowires are provided in segments throughout the substrate surface, wherein the sidewalls of the nanowires of different segments are differently functionalized so as to attach different specific molecules.

In one embodiment, the nanowires are provided in an array with a gradient functionalization in at least one direction along the substrate.

In one embodiment, the substrate has a predefined surface region configured for background signal detection, from which region no light is emitted from any nanowire waveguide end.

In one embodiment, said predefined surface region of the substrate is free from nanowires.

In one embodiment, an opaque cover is provided to suppress emission from nanowire ends in said predefined surface region.

In one embodiment, said sidewall is functionalized by means of addition of a functionalizing element selected from proteins, receptors or molecules, or by coating the nanowire with a lipid bilayer.

According to a second aspect, the invention relates to a molecular detection system, comprising a molecular sensor according to any of the preceding embodiments, configured to be placed in contact with a substance at the front side of the substrate such that the nanowire waveguide is injected into the substance, an excitation device configured to emit light towards the sensor, and a detection device configured to detect light emitted from said nanowire end.

In one embodiment, said excitation device is configured for global excitation by illumination of the substance.

In one embodiment, said excitation device is configured for local excitation by inserting light into the nanowire waveguide.

In one embodiment, said nanowire projects away from the front side of the substrate to a first nanowire end, and is attached to the substrate adjacent to a second nanowire end, wherein the detection device is optically connected to detect light from the second nanowire end from a rear side of the substrate.

In one embodiment, said detection device has a focal plane, and is arranged with said focal plane substantially positioned at said nanowire end through which light is emitted.

In one embodiment, said detection device comprises a planar light detector element, configured in optical contact with said end of the nanowire through which light is emitted.

According to a third aspect, the invention relates to a method for molecular detection in a substance using a nanowire molecular sensor, comprising the steps of providing the substance at a front side of a substrate, such that a nanowire projecting from the substrate is entered into the substance, said nanowire having two ends and a sidewall, which sidewall is functionalized in order to attach a molecule; exciting light emissive point sources at the sidewall, such that light is coupled to the nanowire which acts as a waveguide; and detecting light emitted from an end of the nanowire, wherein the amount of light emitted at the end of the nanowire is dependent on the amount of specific molecules attached to the sidewall.

In one embodiment, said nanowire projects away from the front side of the substrate to a first nanowire end, which is entered into the substance, and wherein the step of detecting light includes detecting light emitted from a second nanowire end, at a rear side of the substrate.

In one embodiment, the substance is contained in a miniscule vessel, which vessel is penetrated by said nanowire.

In one embodiment, said substance is a single biological cell, wherein said nanowire penetrates a cell wall of said biological cell.

In one embodiment, the step of ejecting the nanowire from the substance is carried out before the steps of exciting light emissive point sources and detecting light emitted from the nanowire end.

In one embodiment, the substance is led along the substrate in a microfluidic system.

In one embodiment, predetermined elements are attached to the nanowire, configured to cause a reaction in a cell, wherein said reaction has an effect on the amount of specific molecules attached to the sidewall.

In one embodiment, the method involves using a nanowire molecular sensor according to any of the preceding embodiments in a molecular detection system according to any of the preceding embodiments.

BRIEF DESCRIPTION OF THE DRAWINGS

Further features of the invention and related embodiments will be described with reference to the appended drawings, in which:

FIGS. 11A-11D show various embodiments of measurement setup, comprising an excitation device and a detection device;

FIG. 12 shows a nanowire optical molecular sensor according to one embodiment of the invention where FRET between biomolecules is utilized;

DETAILED DESCRIPTION OF EMBODIMENTS

Optical wave guiding in nanowires is, as such, a well-known phenomenon, as e.g. in U.S. Pat. No. 8,183,587. The wave-guiding properties of a nanowire can be manipulated in different ways. The nanowire core has a first effective refractive index, n1, and, when a shell is present, as optical cladding material surrounding at least a portion of the nanowire core has a second effective refractive index, n2. The surrounding medium (e.g. air or water) has a third refractive index, n0. By assuring that the first refractive index is larger than the second refractive index and the third refractive index, n1>n2>n0, good wave-guiding properties are maintained in the nanowire. When a shell is not present the n1=n2 and good wave-guiding properties are maintained when n1>n0. The wave-guiding properties may be further improved by introducing optically active cladding layers on the nanowire and enhanced by positioning the nanowire in an array of nanowires. The enhancement can be determined by non-trivial relationships between nanowire diameter, shell thickness, spacing, pattern-shape, refractive index and excitation/emission wavelength. On the other hand also systems with n2>n1>n0, n2>n0>n1 as well as n2>n0=n1 show waveguiding in the nanowires. Such systems could represent for example hollow nanowires, so called nanotubes, see Nano Research 5 (3), 190-198, that can be used simultaneously with optical detection also for cell injection. Additionally, the shape of the nanowire can be altered from a straight cylinder, for example into the shape of a tapered cylinder, that is, a cone, to fine-tune the waveguide performance. These variants may also be employed for the nanowire waveguides in the embodiments described below.

Figure 1:
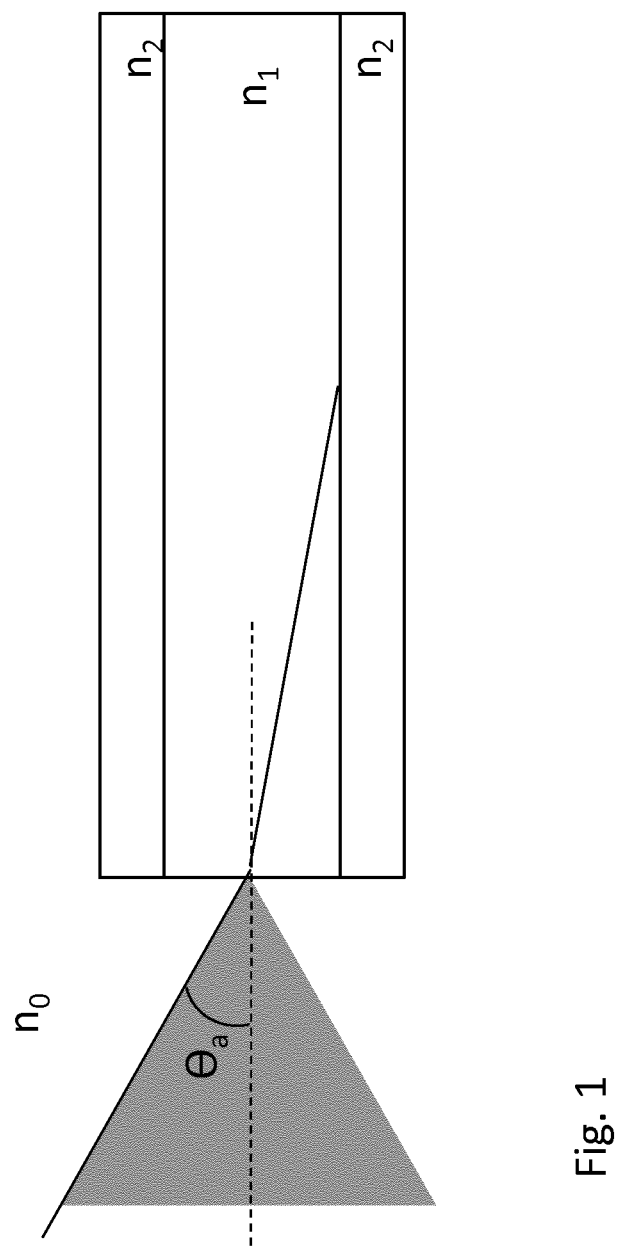
FIG. 1 schematically illustrates a nanowire waveguide where incident light in the acceptance angle is coupled in to the waveguide (prior art)

In a large-diameter conventional waveguide, such as in an optical fiber with a diameter much larger than the wavelength of the light, light is usually injected at the axial end of the waveguide in order to confine it to the waveguide. In such a case, light can be described as rays in geometrical optics, and the incident angle of the light should not be larger than the half cone angle $\Theta_a$ of the acceptance cone, given in the formula for the numerical aperture $$NA = n_0 \sin \Theta_a = (n_1^2 - n_2^2)^{1/2},$$

wherein n0 is the refraction index outside the waveguide, see FIG. 1 (prior art).

Light emitted from the volume surrounding the nanowire sidewalls will usually have incidence angles that do not allow for in-coupling and confinement into such a conventional waveguide. As described below as a distinctive feature of the invention, when the diameter of the nanowire is comparable to the wavelength of light, light can couple by another mechanism to the waveguide due to an optical near-field effect.

Figure 2:
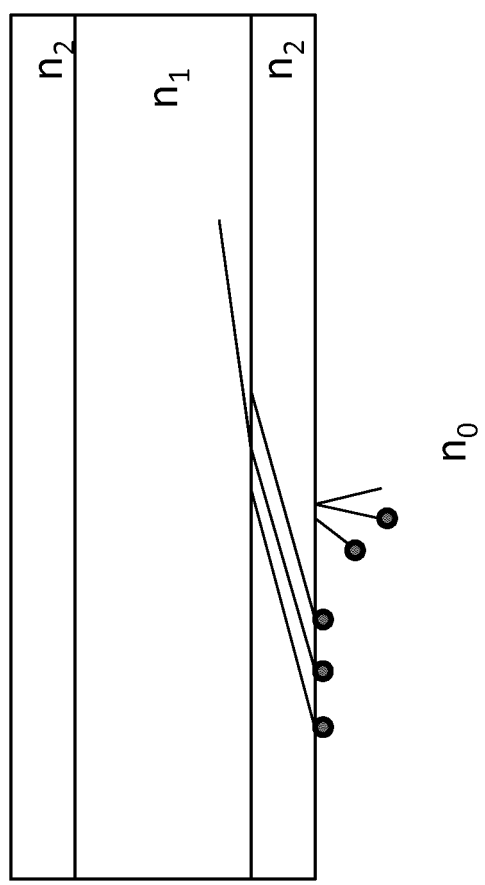
FIG. 2 shows a nanowire waveguide where light is coupled in at the sidewall from SALEPS, according to an embodiment of the invention.

As indicated above, a first distinguishing feature of the invention is a near field (NF) or fluorescence resonant energy transfer (FRET) coupling mechanism between point light sources and a nanowire waveguide to only allow light emitted in the absolute proximity of the nanowire side-surface to be coupled into the nanowires so as to subsequently be connected to reach a detector, such as a camera or an eye. Such light coupling is schematically illustrated in FIG. 2.

Light from surface attached light emissive point sources (SALEPS) on the nanowire sidewall or in its immediate vicinity can be coupled directly to a wave-guiding mode in the nanowire. This is explained by a coupling between the point source and the near field (NF) of a wave guiding mode of the nanowire. The efficiency of this coupling is dependent on the NF of the wave guide mode at the location of the point source. The NF profile of the wave guide mode can be tailored by varying, through non-trivial relationships, the nanowire diameter, shell thickness, spacing, pattern-shape, refractive index and wavelength of the light. In this way, by confining the NF of the wave guide mode to the vicinity of the nanowire, spatial selectivity in the coupling from the point source to the wave guide mode can be obtained: Only point sources within the extension of the NF of the wave guide mode can couple to the wave guide mode. For example, the NF of the fundamental HE11 wave guide mode can show localization to a distance of less than $\lambda/10$ outside the nanowire [inset of FIG. 4d in Nano Res. 2012, 5(12): 863-874]. After such excitation of the wave guide mode, the light in the mode can propagate toward the top and bottom facets of the nanowire where the light can couple out to the optical far-field where it can be detected with conventional optical setups, as observed in Nano Lett., 2014, 14 (2), pp 737-742.

Similar effects could also potentially be invoked through fluorescence resonant energy transfer (FRET) or sequential absorption and reemission of light if the nanowire is a direct bandgap semiconductor. By collecting the light exiting from one end of the nanowire waveguide, light emitted from point sources along the surface of the nanowire can be detected in one focal point, and for a nanowire array, in one focal plane. The effect is further shown to have a direct linear relation between the number of point sources and the light exiting the nanowire end, as exemplified in FIG. 4 of the mentioned Nano Lett. paper.

A second distinguishing feature of the invention is that the surface whereon the selection is performed is a nanowire sidewall.

The selection and attachment process can be enabled by chemical functionalization of the nanowire sidewall so that molecules of a specific type are prone to attach to the surface while other types of molecules remain in solution or gas phase. Functionalizing elements can be chosen from a wide group of proteins, receptors and molecules (Sperling and Parak, 2010 (368), Phil. Trans. R. Soc. A). The nanowire may also be coated with a lipid bilayer for detection of molecules (for example lipids or proteins) embedded into the bilayer or attached to the bilayer.

Figure 8:
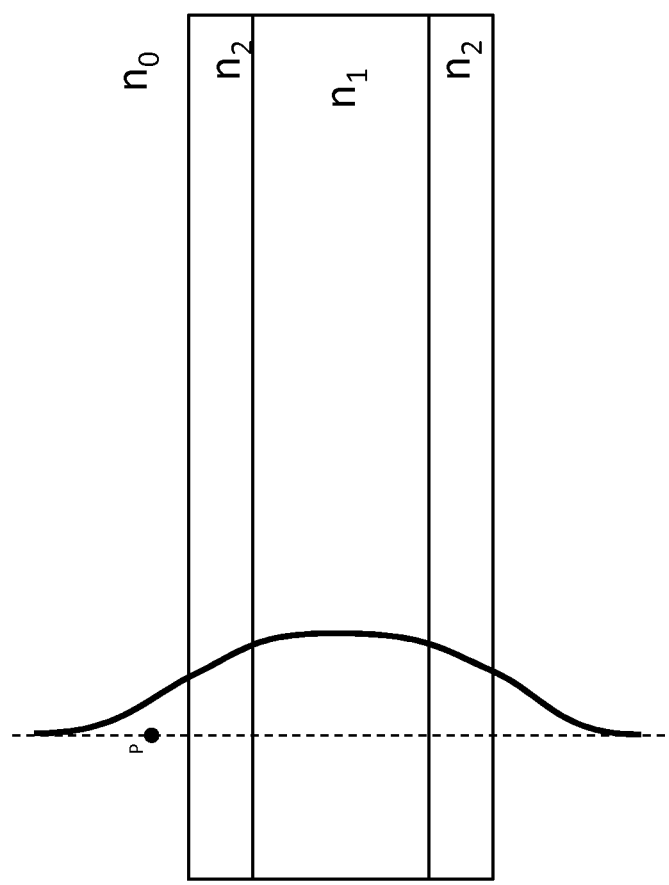
FIG. 8 illustrates a nanowire waveguide where light from a point dipole P couples into the wave guide mode of the nanowire, with depicted spatial profile of the optical near field.

The excitation of a wave-guiding mode is a short distance effect, decreasing rapidly over a few nanometers in the case of FRET, and, for NF, over a distance that can be a fraction of the wavelength, $\lambda$, of the light emitted by the SALEPS. Therefore, the SALEPS must be bound to a point that must be less than $\lambda/2$ (preferably less than $\lambda/10$) from the nanowire surface. Accordingly, all embodiments include alternatives wherein the SALEPs are bound to a point that may be less than $\lambda/2$, $\lambda/4$, $\lambda/8$, or $\lambda/10$ from the nanowire surface. A rationalization of these relative numbers comes from the fundamental physical understanding of the process: If we assume the HE11 waveguide mode coupling occurs, the HE11 waveguide mode is similar to a plane wave localized outside of the nanowire. The mode shows therefore extremely slow decay away from the nanowire for small diameters (effective diameters coming from a combination of the core and shell materials). For a large diameter, the HE11 mode becomes completely bound to the nanowire and should leak very weakly to the outside of the nanowire. In this fashion the strength of coupling, depending on the distance to the nanowire surface, can be set as a function of the dimensions of the nanowire array, specifically for a given mode. FIG. 8 illustrates an example of a nanowire according to one embodiment, tailored such that a point dipole P located close to the nanowire sidewall couples into a wave guide mode of the nanowire, with depicted spatial profile of the optical near field.

It's important to note that, even if the method in one preferential embodiment is to be used where excitation light shines globally on the nanowire array sample, the optical near-field is not necessarily homogenous at all locations inside the nanowire array due to near-field effects. For example, incident light can couple strongly into a waveguide mode. In that case, the near-field of the incident light can be strongly localized to the vicinity to the nanowire surface. In principle the waveguide modes in nanowires are just natural optical modes of the system, similar to the surface plasmons in conventional metallic systems, and they can affect both the incoupling/localization of the near-field of globally incident light as well as the emission properties of light emitters in the vicinity of structure.

On the other hand, it is possible to combine different effects to tune the in-coupling of light into the nanowires. For instance, the surface chemistry of the nanowire can be modified, not only to allow specific binding of recognition molecules, but also for quenching of fluorescence very close to the surface, or for exciting surface enhanced raman scattering (SERS) to detect the degree of direct surface adsorption. In this way, it is possible to appropriately tune the nanowire internal properties and surface chemistry effects in order to optimize the optical coupling efficiency of light into the nanowires for molecules that are at a distance from the surface expected for the secondary specific recognition molecules mentioned above. This distance is expected to be in the range of 2-200 nm from the surface. Light emission from fluorophores adsorbed directly to the surface would, on the other hand, either be suppressed, e.g. quenched, or the amount of directly adsorbed fluorophores would be detected, e.g. by SERS, for subsequent subtraction of the surface adsorbed signal from the total signal from the sensor.

The above paragraph can be summarized to apply to a nanowire molecular sensor where the nanowire internal properties, including chemistry and geometry of core and shell, are tuned to the surface chemistry to optimize light collection at different distances, in the range 2-200 nm, away from the nanowire sidewalls.

Figure 3:
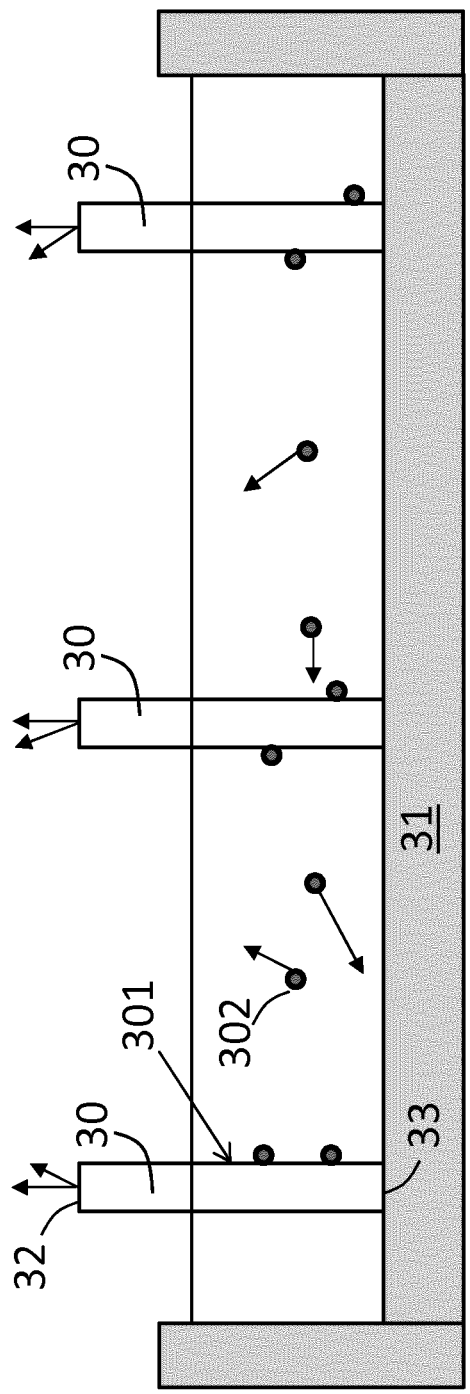
FIG. 3 shows a nanowire waveguide array in fluidic solution, according to an embodiment of the invention.

In one embodiment, as indicated in FIG. 3, the molecular sensor comprises a plurality of nanowires 30, arranged in a mutually parallel pattern or array on a substrate 31. Each nanowire 30 extends from a front side (upper side in the drawing) of the substrate 31, and has two opposing ends 32, 33 and a sidewall 301 there between. The nanowires 30 project away from the front side of the substrate 31 to a first nanowire end 32, and is attached to the substrate adjacent to a second nanowire end 33. In the embodiment of FIG. 3, each nanowire 30 is attached at its second end 33, but other configurations are included in various embodiments, as will be explained, where the second end 33 ends or even projects from a rear side of the substrate 31. In this drawing, the molecular sensor is at least partially submerged in a substance to be analyzed, which is a fluid containing particles 302. The particles 302 may attach, or at least be located close, to the side surfaces 301 of the nanowires, at which light emitted may be connected into the nanowires and propagate therein for emission through at least one end 32 or 33 of the nanowires 30. The emission of light may be obtained in different ways, e.g. by attaching of a light-emitting particle to the side surface, or by interaction between particles (molecules) and a functionalized nanowire side surface carrying potentially light-emitting molecules, so as to cause such potentially light-emitting molecules to either start or stop emitting light.

Figure 4C:
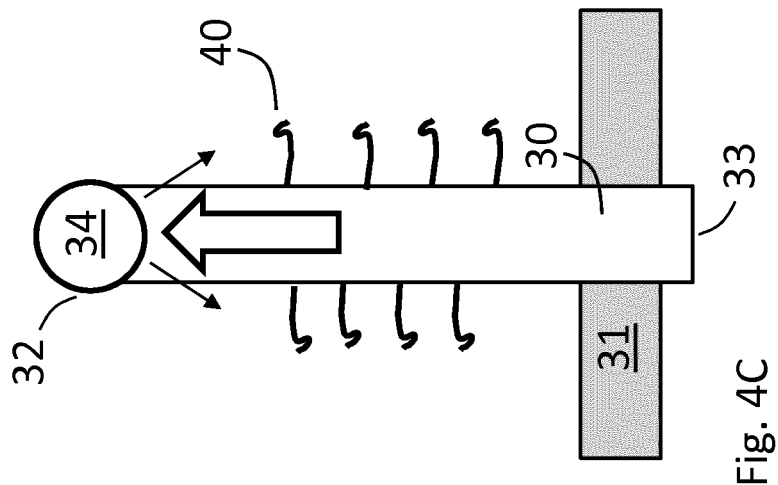
FIGS. 4A-4C illustrate nanowires with a functionalized surface, according to various embodiments of the invention.
Figure 4B:
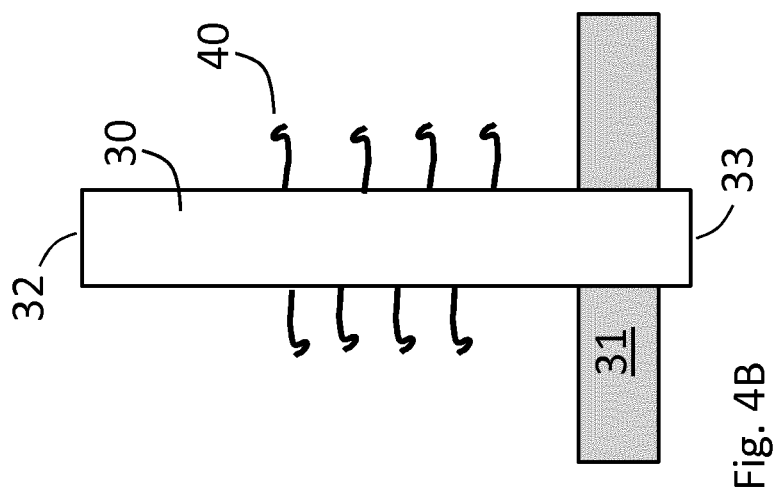
Figure 4A:
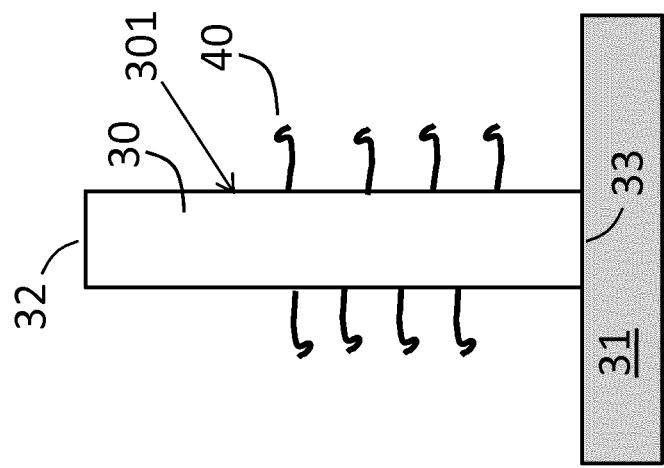

One way of obtaining this effect is by means of a third distinguishing feature of the invention, is given by the introduction of a phosphorous molecule, such as a fluorophore, functioning as a light emissive point source (Zamai, M., Malengo, G. & Caiolfa, V. R. in Biophotonics Biological and Medical Physics, Biomedical Engineering (eds Lorenzo Pavesi & PhilippeM Fauchet) Ch. 10, 177-197 (Springer Berlin Heidelberg, 2008)). In one embodiment of the invention, as depicted in FIGS. 4A-4C, the nanowire sidewall is functionalized 40 (visualized by means of hooks representing molecular bonds) such that it is possible for SALEPS to attach to the sidewall.

Figure 5:
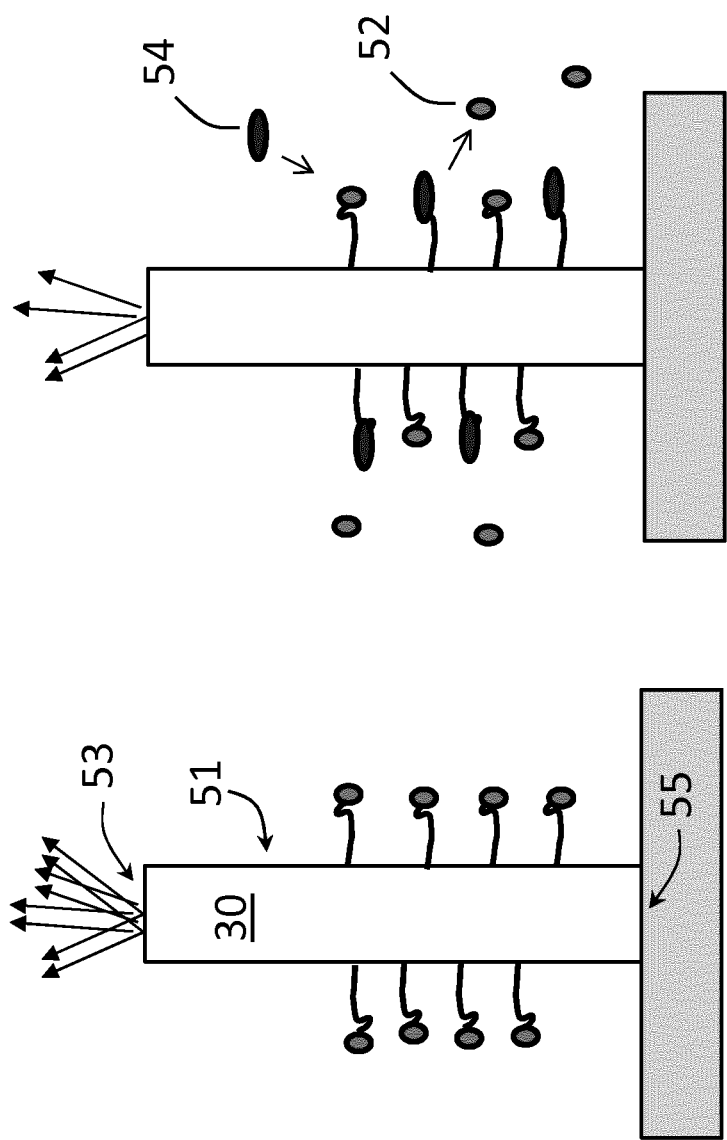
FIG. 5 shows one nanowire of an optical molecular sensor according to an embodiment of the invention.

FIG. 5 shows an embodiment to the left, where SALEPS 52 are attached to a sidewall 51 of a nanowire 30. Light emitted from the attached SALEPS 52 is coupled into the nanowire 30, acting as a waveguide, and subsequently emitted at an end 53 of the nanowire 30. To the right in the drawing, specific molecules 54 can attach to the surface and release or replace the SALEPS 52, and in this way, decrease the density of SALEPS, as illustrated in the decreasing light from the nanowire end 53.

Figure 6:
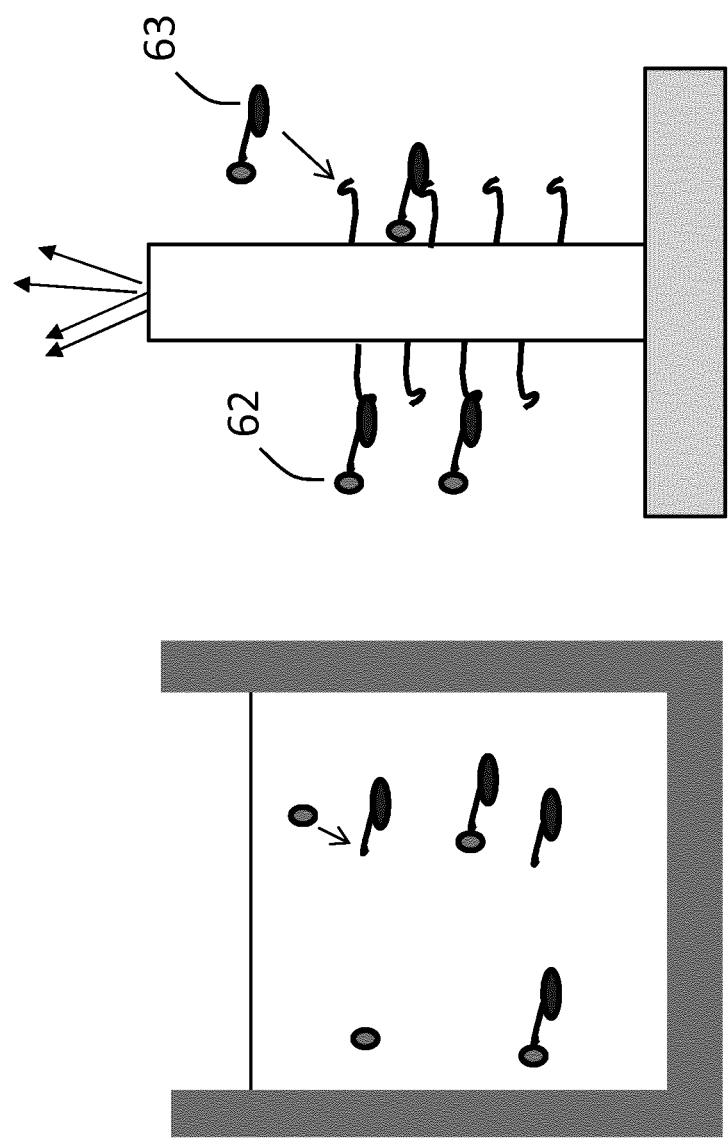
FIG. 6 shows one nanowire of an optical molecular sensor according to an embodiment of the invention.
Figure 7:
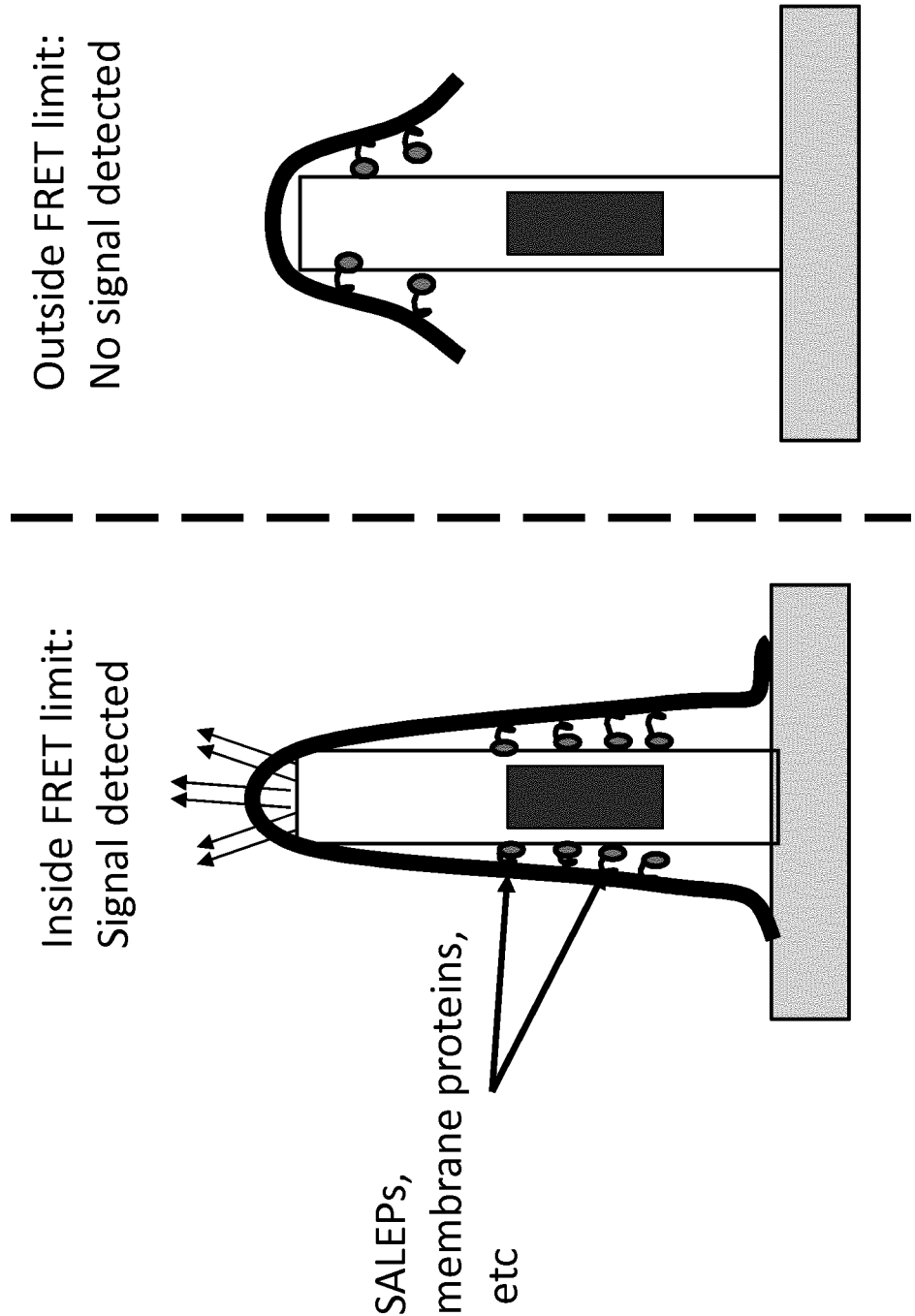
FIG. 7 shows a nanowire optical molecular sensor and a membrane according to one embodiment of the invention.

In one embodiment the nanowire sidewall may be pre-functionalized with SALEPS 52 attached to the sidewall, which are quenched (in a dark state). When specific molecules attach to the surface they un-quench the SALEPS, allowing them to fluoresce, thus increasing the density of unquenched, light emitting SALEPS at the surface over time. In yet another embodiment, as depicted in FIG. 6, fluorophore molecules 62 are attached by chemical means to a linker molecule 63, and when the linker molecule is attached to the nanowire surface the density of surface attached light emissive point sources (SALEPS) is increased.

Returning to FIGS. 4A-4C, nanowire designs are shown, that may be employed in the embodiments described herein. As opposed to FIG. 4A, the nanowire 30 of FIG. 4B has its second end located at a rear side of the substrate 31. This design makes it possible to detect light coupled to the nanowire wave guide 30 through its sidewall 301, emitted through the second end 33 of the nanowire, at the rear side of the substrate. In addition, or alternatively, excitation of SALEPS connected to or present close to the sidewall may be carried out by means of injection of light from the second end 33. FIG. 4C describes an embodiment with another feature, namely a nanowire end member 34, e.g. a particle used as a catalyst for growing the nanowire 30, e.g. a gold droplet, or a particle attached after growing the nanowire 30. This nanowire end member 34 may effectively distribute excitation light injected through the second nanowire end 33 in addition to, or as an alternative to, nearfield coupling through the sidewall 301, so as to assist in excitation of SALEPS in the vicinity of the nanowire sidewall, as indicated by arrows in the drawing. Conversely, light emitted from excited SALEPs in the near vicinity of the nanowire sidewall 301 may be coupled into the nanowire waveguide, for subsequent detection at the second nanowire end 33, without such SALEPs having to be attached to the nanowire sidewall 301.

Figure 9B:
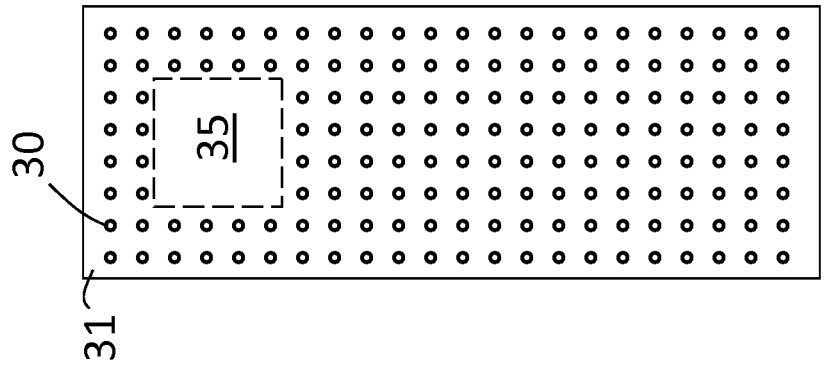
FIG. 9B shows a top view of an array of nanowires, in which a region is configured for background level detection.

SALEPS can be detected statistically by the means of a light-detector, for example, a charged coupled device (CCD camera) as in standard fluorescence microscopy. However, as shown in FIG. 2, the detection resolution is usually obscured in several ways, such as the presence of a liquid or gas phase solution and stray phosphorous molecules in the vicinity, and also by inability to extend the optical focal plane beyond a certain length of the nanowire surface. By near-field coupling of light from the SALEPS to the nanowire waveguide, statistics can be extracted from a focal plane separate from the physical location of the SALEPS and undisturbed by their environment. At the same time, stray phosphorous molecules contribute to a flat background level which can, if necessary, be monitored and corrected for by measuring on a nanowire-free region of the nanowire detector. In one embodiment, as shown in FIG. 9B, this flat background may be monitored and corrected for by measuring on a region 35 on the substrate 31, which is free from nanowire end light emission. This region 35 may be nanowire-free. This can be accomplished by not growing any nanowires 30 in that region 35, or by removing nanowires from that region 35. Alternatively, a substantially opaque cover may be provided over nanowires 30 in that region 35 to suppress emission from nanowire ends that surface region 35.

Furthermore, the usual global detection of fluorescent molecules in the sample cannot selectively distinguish bound target molecules from unbound target molecules, or from any other molecules in the solution that also emit fluorescent light of a similar wavelength, unless global detection is combined with selective excitation, for example using TIRF.

One novel feature of the invention can thus be illustrated by comparison to the widely used TIRF method: TIRF uses the NF effect to optically excite only molecules in a specific target volume, but then detects all fluorescence coming from the sample globally. In comparison, our invention uses global fluorescence excitement and detects enhanced surface bound fluorescence using the NF effect, enabled by the specific nanostructured surface used for the sensor, thereby filtering out potential fluorescence from the environment. Alternatively, it is possible to filter out fluorescence from stray phosphorous molecules by monitoring emission from a nanowire-free region of the nanowire detector as described with reference to FIG. 9B. However, whereas TIRF requires a specialized optical setup for excitation, to achieve total internal reflection, the present invention can use a standard optical set-up for excitation and detection, as visualized in FIG. 11. In summary, TIRF uses selective excitation and global detection, this method uses simpler, and more efficient, global excitation and achieves enhanced selective detection, determined by a specific surface structure and topology.

A second advantage compared to the TIRF technique is the much enlarged detection surface, and thus detection sensitivity, offered by a nanowire array compared to a flat surface. In addition to the simplifications inherent in detection using the current invention compared to e.g. TIRF, there are two very important advantages of the present method compared to a range of conventional, non-TIRF based FLISA and microarray methods.

Thus, the method described here
- circumvents the problem of non-specific background fluorescence in solution by the combination of a large surface area to volume ratio of the nanowire detector and point-wise emission of light at the nanowire tip from all analytes specifically bound to the detector surface but suppressed signal from analytes in solution. In addition, analytes in solution of a substance to be analyzed may contribute to a flat background, as described with reference to FIG. 9B;
- circumvents the effect of secondary recognition elements non-specifically adsorbed directly to the nanowire surface by adjusting the nanowire structure and chemistry to the expected distance of the secondary recognition molecule from the nanowire side-wall to allow maximal in-coupling of light into the nanowire of fluorophores located at this distance;
- allows the use of topological enhancement of the effective detection surface area (using nanowire arrays) while still allowing optical readout from a single focal plane.

In principle the wavelength of the exciting light can be used as a free probing parameter for a given fabricated system. An excitation wavelength can be off-resonance so that the excitation is not localized to the surrounding of the wires. In a similar fashion one can utilize an excitation wavelength that is at the resonance of the nanowires where light is localized to the surrounding of the nanowires. In this way, by optimizing the geometry of the nanowires, the enhancement of excitation-light into the waveguides can occur automatically for globally incident light.

In another embodiment of the invention, the nanowires' wave-guiding properties are used to guide the excitation light only along the nanowires, and molecules in the vicinity of the nanowire surface are excited by the NF effect enabled by the nanowire geometry, while detection is globally. This can be used to selectively excite different areas, functionalized in different manner in order to attach different elements or molecules. This can be used to increase the ratio of detected light from SALEPs attached to the nanowire surface and SALEPs in solution. Furthermore, it can facilitate excitation of SALEPs at the surface when working with opaque solutions.

Specifically, methods currently used to print certain types of oligonucleotides into micrometer sized spots in microarrays on a flat surface could be used to print different oligonucleotides onto micrometer sized areas with a large number of nanowires e.g. in arrays. The resulting nanowire-enhanced microarrays leads to an order of magnitude higher surface area, as compared to FRET, for binding of the target oligonucleotide analyte without increasing the footprint for fluorescence detection. Therefore, obtaining similar densities of detection spots is possible as in conventional microarrays. Finally the signal-to-noise ratio of the microarray is increased in proportion to the surface-footprint area ratio enhancements as the fluorescence from all fluorophores at the nanowire sidewalls is emitted from the nanowire tips.

In addition, NEMO-microarrays could be used with developing microfluidic technology to enhance resolution in, for example, titration experiments. Where instead of using discrete micrometer spots, one could use a continuous gradient of solute to initially functionalize the NEMO-microarrays and subsequently rinse with the analyte. The result would be a continuous concentration gradient test with discrete fluorescence readouts at each row of nanowires perpendicular to the initial gradient, where, due to the increased surface area, it would be possible to obtain sufficient fluorescence readout signal from each nanowire tip. The reliability of the functionalization and readout can be confirmed using multiple wires as repeats, since a typical density of wires is on the order of $1/\mu m^2$.

In one embodiment the nanowire array is removed from the original substrate and embedding the lower parts of the nanowires in an matrix of lower optical refraction index where the matrix of lower optical refraction index and the lower parts of the nanowires can be said to form a new substrate or be mounted on a new carrier substrate. Similar techniques can be used to fabricate flexible, bio-compatible, devices for application where such are advantageous. In order to minimize stray excitation in the environment an opaque layer can be deposited on the surface of the substrate surface, between the nanowires.

Various features, alternative embodiments and benefits of the invention are outlined above and below. Different embodiments of the invention may be industrially applicable in various fields of technology, such e.g. as in biomedical processes, DNA analysis, gas detection, pollution detection, ion detection, and even for characterization of functionalization techniques. Some more specific examples of application are given below.

A sensor according to the invention can be used to detect oligonucleotides, proteins, lipids, or microorganisms in any type of body fluid such as blood or fractions thereof, saliva, urine or interstitial fluid.

A sensor according to the invention can be used to detect proteins, lipids, metal ions or microorganisms for environmental monitoring e.g. in sea water, freshwater or extracts from soil.

A sensor according to the invention can also be used to detect aerosols, molecules, such as hydrides and other harmful gases in air. It can also be used to detect impurities, such as oxygen, and water in nitrogen glove box environments.

A sensor according to the invention can for example be used to detect membrane proteins or other molecules that attach to lipid bilayers, by coating the nanowires with a lipid bilayer (prior art, Dabkowska et al., accepted by Nano Letters).

A sensor according to the invention can be used to monitor the activity of enzymes, for example by selectively attaching substrate molecules to the nanowire surface, and monitoring the enzyme activity as a change in light emission from the nanowire ends as a result of enzyme activity. This can be achieved, for example, by using either a quenching or unquenching effect that will decrease or increase fluorescent emission from the target substrate molecule as a result of enzymatic action.

A sensor according to the invention may be used to detect target molecules in extremely small volumes, such as single biological cells, by inserting an array of functionalized nanowires or a single functionalized nanowire as a probe into the sample volume. While the nanowires are inserted into the sample volume, or after removal from the sample volume, the integrated fluorescence from all target molecules attached to the wires can then be detected optically by detecting the emission from the nanowire(s) top(s). For example, the method may be used to detect specific mRNA in individual living cells, by coating the nanowire with short strands of complementary single-stranded, DNA oligomers and inserting one or more nanowires into the cell. After removal from the cell, hybridized DNA (indicating the presence of mRNA) are made fluorescent (for example using an intercalating dye, or another method) and optically detected as described above.

Figure 10A:
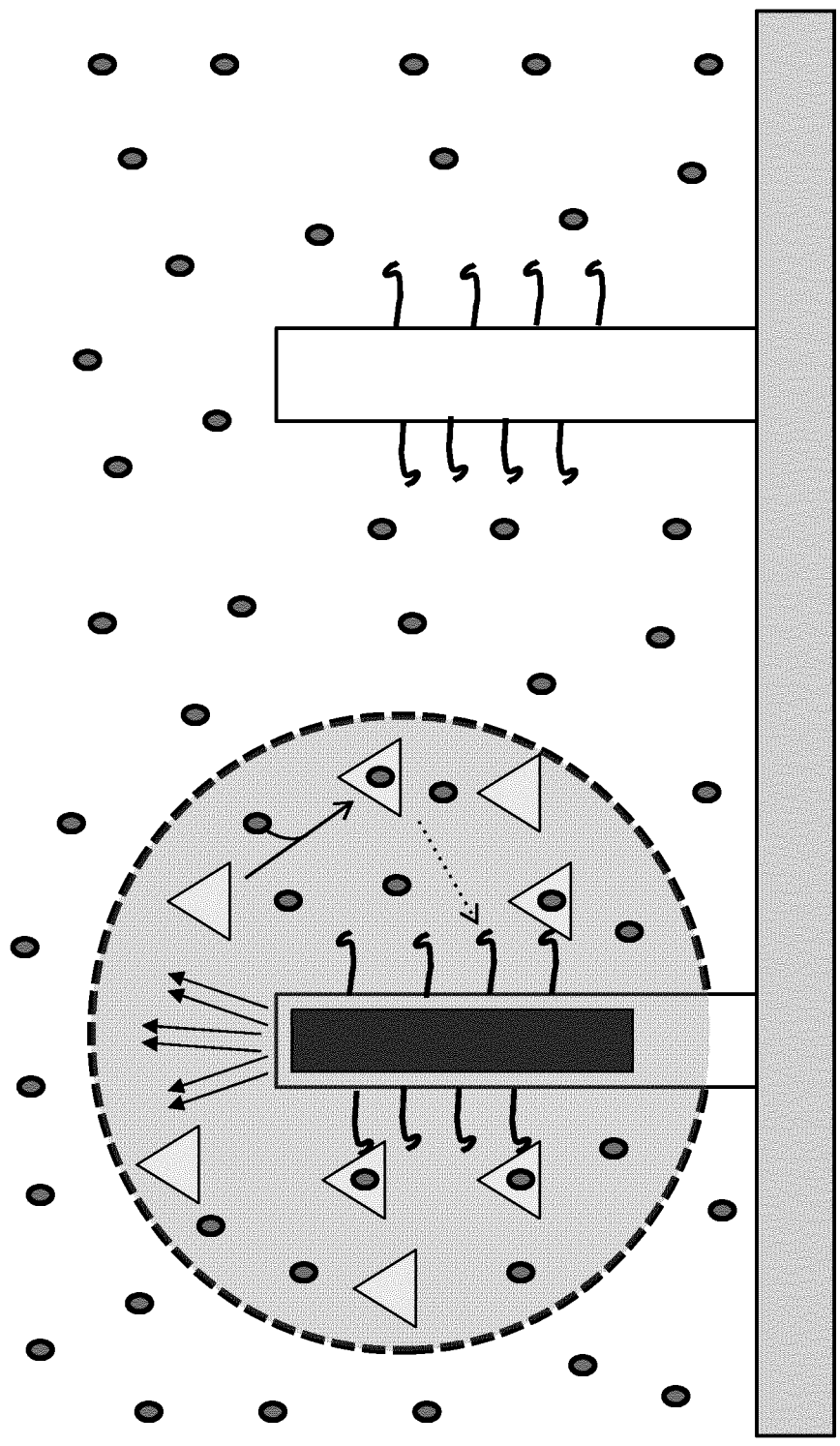
FIG. 10 shows a nanowire array where one nanowire waveguide is immersed in a micro-volume vessel to locally detect small amounts of a target analyte (here a reaction product) formed in the micro-volume vessel.
FIGS. 10B and 10C illustrate alternative embodiments of the setup of FIG. 10A.

A sensor according to the invention may be used as an insertable tool in nano- or micro-reactors, such as, polymerosomes, protein cages, microemulsions, virus capsids, micelles, giant lipid vesicles or other nano- or micro-vessels (see FIG. 10A). It may also be used to detect chemical concentrations or concentrations of biomolecules in living cells. With or without surface modification, the device is capable of being inserted into a miniscule vessel for the detection of local concentrations, the delivery of a specific molecule, the separation of reactants and products, or the provision of a catalytic surface. The devices may be multi-functional in these aspects. The near-field signal amplification attained by the device could improve detection of the small amounts of target analytes contained in these low-volume vessels. The device surface may be roughened or chemically modified or functionalized to aide device insertion, or the adsorption and/or binding of molecules.

FIGS. 10B and 10C illustrate embodiments that are examples of the embodiment of FIG. 10, in terms of construction and use. These drawings indicate a functionalized sidewall 301, which as such may be achieved in any of the embodiments described herein by e.g. preparation of the sidewall 301 with functionalizing elements or by coating the nanowire with a specific lipid bilayer.

FIG. 10B illustrates a scenario where one (or more) nanowire, configured to act as a waveguide, penetrates a miniscule vessel, such as an organic cell 110 and potentially even a living single cell. The nanowire 30 sidewall 301 is functionalized so as to attach specific molecules, indicated as dots in the drawing. An excitation device 101, here exemplified as a global excitation lamp, illuminates the penetrated cell such that SALEPs emit light, which is coupled through the sidewall 301 of the nanowire 30, which acts as a waveguide to emit the coupled light through a nanowire end. In the given example, emission is directed out from the second (bottom) end of the nanowire, at a rear side of the substrate carrying the nanowire, opposite the front side where the substance vessel 110 is arranged. As described, the light detected from the end of the nanowire 30 will be dependent on the amount of molecules attached to its sidewall 301. As outlined with reference to FIGS. 3-7, SALEPs may be configured to emit light by means of the character of the connection to the functionalized sidewall 301. Alternatively, the sidewall may be pre-characterized with SALEPs on the sidewall 301, which may be released, or un-quenched, upon the connection of the specific molecules to the sidewall 301. Other ways of configuring the nanowires such that the amount of light emitted from the nanowire end is dependent on the amount of molecules attached to, or located in the near vicinity of, the sidewall 301 are possible.

FIG. 10C illustrates a variant of this embodiment, for detecting presence and/or concentration of certain specific molecules in e.g. a cell. In this embodiment, vessel penetration is carried out to attach the specific molecules to the nanowire, where after the nanowire is ejected from the vessel 110 before excitation and detection of coupled light transported in the nanowire waveguide 30 is carried out. These steps of excitation and detection may also be preceded with an additional preparation step, for binding fluorescent markers to the nanowire sidewall, e.g. by subjecting the substrate to a solution of such markers. Such markers may e.g. be configured to attach to the specific molecules attached from the vessel 110, or to functionalization elements 40 on the sidewall 301 where no specific molecules have attached, or to release the specific molecules. Nevertheless, the excitation and detection will yield a light output that is dependent on the amount of molecules attached to the sidewall surface 301. A benefit of the sensors of the embodiments herein, for the purpose of miniscule vessel analysis, such as cell investigation, is that it may be employed for detection of the presence of specific molecules and chemicals in the cell, or even observing enzymatic activity and chemical reactions in the cell. In one embodiment, predetermined elements may be attached to a nanowire 30, such as to sidewall 301 of the nanowire, configured to cause a reaction in a cell. Such predetermined elements may e.g. be enzymes or other catalysts, antibiotic elements, proteins, hormones etc. When the nanowire thus configured penetrates a cell, the attached predetermined element may be configured to be released from the sidewall 31, or alternatively remain on the sidewall, and nevertheless cause a reaction in the cell. In one embodiment, the nanowire sidewall 301 is further functionalized such that attachment of specific molecules, release of molecules, or de-quenching of molecules at the sidewall 301, will affect light emitted from SALEPs at the sidewall 301, upon excitation, in accordance with any of the embodiments described herein. This way, the nanowire molecular sensor may be used to cause a reaction in the cell, and to monitor said reaction in real time, even within the cell, or after ejection from the cell.

Figure 11A:
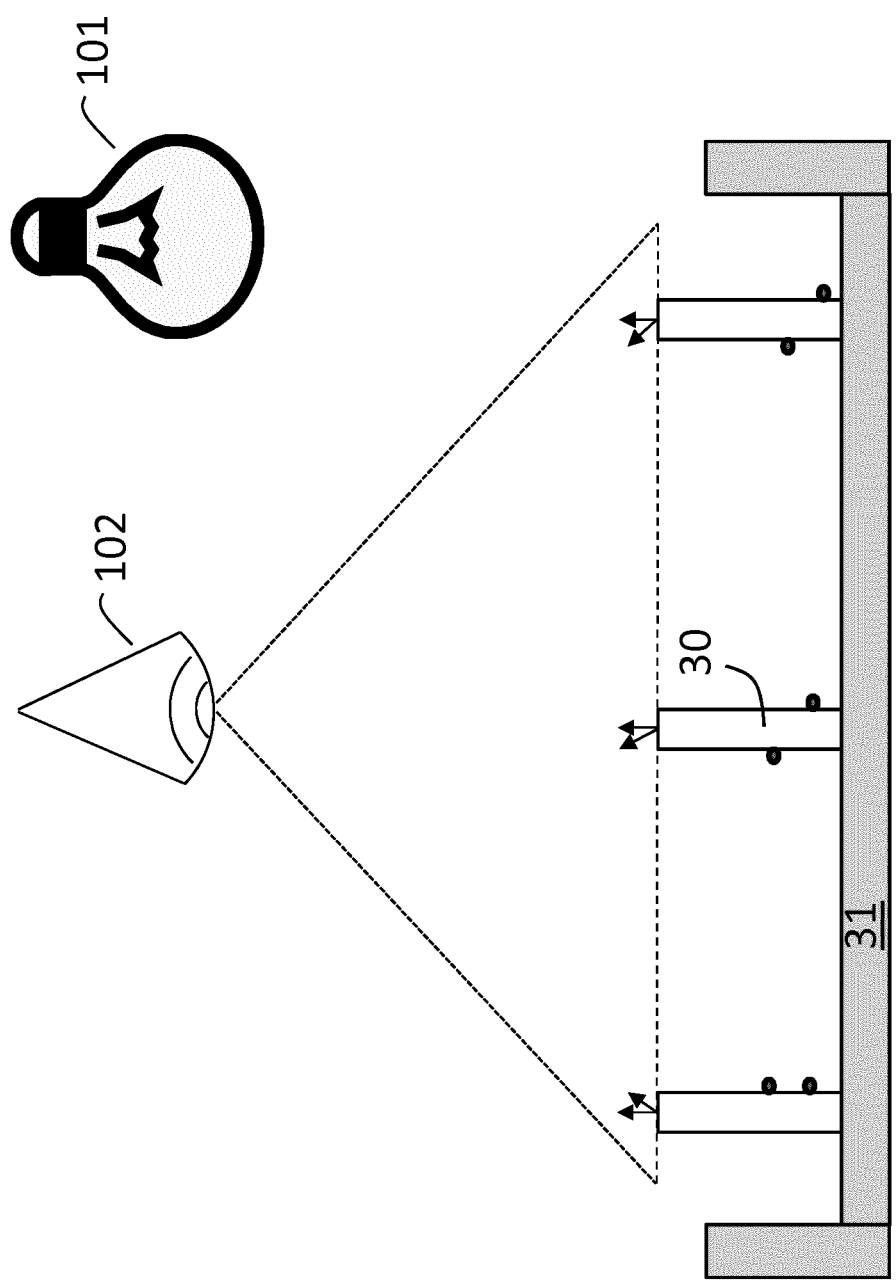

A brief description of FIGS. 11A-11D will now be provided, so as to indicate different configurations for excitation and detection of light, in a molecular detection system comprising a molecular sensor according to any of the embodiments described herein. In FIG. 11A global excitation is carried out, e.g. by means of a lamp 101, arranged to illuminate a front side of the substrate 31. Such a setup may be employed for transparent substances (not shown) to be analyzed. Furthermore, detection of light emitted from the nanowire waveguides 30 is detected by means of arranging a detecting device 102 such that a focal plane thereof aligns with the ends of the nanowires from which the light is emitted. In this example, the nanowires are configured to emit only from the first (upper) ends. The detecting device may e.g. be a microscope, or a camera.

FIG. 11B illustrates an alternative embodiment, where the detection device 102 is optically connected to the light-emitting ends of the nanowires 30, in this example the first ends 32 opposite to the substrate 31. The detection device 102 may comprises a planar light detector element, such as a CCD camera, configured in optical contact with said end of the nanowire through which light is emitted, possibly with intermediate transparent optical connector layers. The excitation device 101 may be configured to illuminate the sensor from the side, as illustrated, or e.g. from below, through the substrate 31, if the substrate is transparent. Alternatively, the excitation device 101 may be configured to inject light through the second (lower) ends 33 of the nanowire waveguides 30, by configuring the nanowires to extend to the rear side of the substrate as in FIG. 4B or 4C.

FIG. 11C illustrates yet an alternative embodiment, where the detection device 102 is optically connected to the light-emitting ends of the nanowires 30, in this example the second ends 33 at the rear side of the substrate 31. The first ends 32 of the nanowires may be configured not to emit any light, so as to concentrate emission in the direction of the detecting device 102. The detection device 102 may comprises a planar light detector element, such as a CCD camera, configured in optical contact with said end of the nanowire through which light is emitted, possibly with intermediate transparent optical connector layers. The excitation device may be configured to illuminate the sensor from the side or, as illustrated, from above. A molecular detection system according to FIG. 11c has the benefit of suppressing background noise, if the substrate 31 is substantially opaque.

Figure 11D:
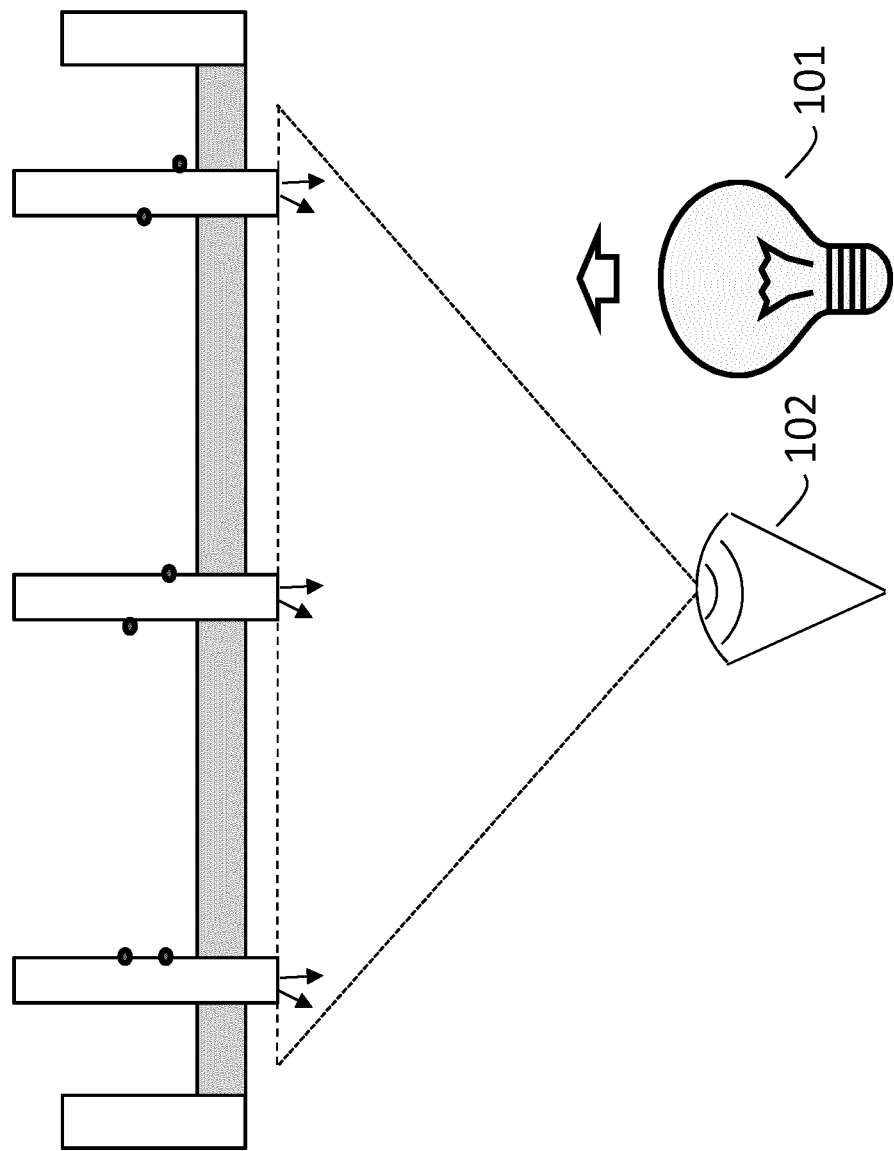

FIG. 11D also illustrates an alternative embodiment, where both excitation and detection is carried out from the rear (lower) side of the substrate, opposite the front side of the substrate 31 where the substance to be analyzed is provided. In this embodiment, both excitation and detection light is transferred through the second (lower) ends 33 of the nanowire waveguides 30. Different methods separating excitation light and detection light are plausible, and since the excitation light is always of higher energy than the detection light, spectral filtration is possible for ensuring that only light emitted from the nanowires 30 is detected in the detecting device.

Other combinations of global and local (nanowire end specific) excitation and detection are plausible within the scope of the invention described herein.

A sensor according to the invention may be improved further by implementing axially grown nanowire heterostructure as the core material having segments with a direct band-gap excitation (Adolfsson, K. et al Nano Lett 2013), as a way to investigate other fluorescent techniques, such as FRET with fluorescently labeled cell membranes, proteins in this membrane (Silvius, J. R.; Nabi, I. R. Mol. Membr. Biol. 2006) or localization of SALEPs for a more controlled sensing approach. The heterostructure nanowire could be coated with an oxide shell and the surface of the nanowire could be coated with SALEPs, which would only be excited by the fluorescence emission of a segment of the nanowire. The fluorescence emission of these surface SALEPs would then be coupled into the nanowire and could be detected at the tip of the wire. In another FRET-based approach, the SALEPs on the surface of the nanowire could be used to excite other SALEPs, which extend just beyond the nanowire surface in a membrane (or in membrane proteins). The emission of these tertiary excited molecules could be coupled into the nanowire and emitted at the tip. An important key to the utility of this approach is that the positioning of the fluorescent segment can be well controlled. By exploiting the fluorescent properties of axial nanowire heterostructures previously demonstrated for biological barcoding (Adolfsson, K. et al Nano Lett 2013), combined with an appropriate shell material, information of the specific position of SALEPs, the cell membrane, or membrane proteins can be distinguished. Such a method would be useful in the sense that one could investigate the possible penetration of a wire into a cell or into the nucleus, for cell injection studies (VanDersarl, J. J., et al. Nano Lett 2011; Persson, H. et al. Nano Res. 2012; Shalek, A. K. et al. Proc. Natl. Acad. Sci. 2010), determined by fluorescent molecules, labeled along the exterior wall of the cell. If for example a wire has broken through the membrane or if the membrane is fully or partially wrapped around the wire, as illustrated in FIG. 6, the use of fluorescent nanowires would allow for a simple optical check to see if molecules could be injected into a cell, without the need for tedious and time consuming transmission electron microscopy or focused ion beam milling of the cell. The configuration would also allow for the possibility to probe cell membrane proteins and possible activity (Maurel, D. et al. Nat Meth 2008).

By introducing an axial semiconductor heterostructure, specifically one with lower bandgap than the rest of the nanowire, positional information by local excitation can be obtained. Examples of such well-known combinations being InAs(P)/InP, GaAs/GaP, InGaP/GaP or InGaN/GaN. One advantage of such structures is that they emit light at specific wavelengths and absorb light below specific wavelengths, determined by their bandgap. In this way, an axial heterostructure, such as a quantum well, can be used as a filter of guided light lower than a specific wavelength or a point emitter of light of a specific wavelength, which can excite the SALEPs in its immediate surroundings. Axial heterostructures are in this way useful in order to obtain information of concentrations inside such low volume vessels, described above in point 7 and, specifically establish when a membrane of a low volume vessel is penetrated and obtain detection of concentrations inside the vessel.

FRET between biomolecules could also be used. The surface of the nanowires could be functionalized with specific molecules (proteins, ssDNA . . . ) labeled with acceptors and the molecules to be detected could be labeled using a donor molecule. Upon binding of the molecule of interest, the FRET signal would be increased (FIG. 12).

Figure 13:
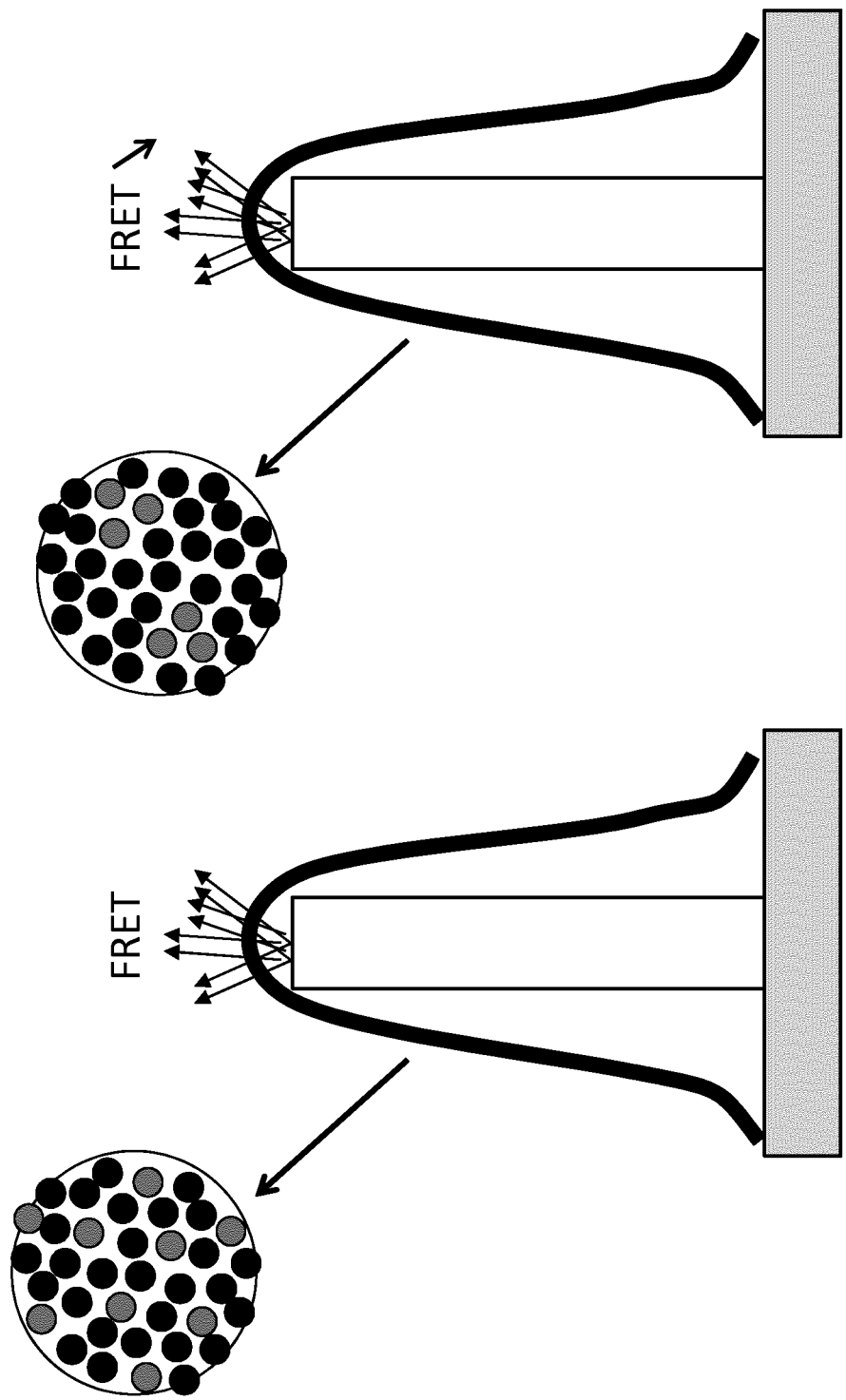
FIG. 13 shows a nanowire optical molecular sensor according to one embodiment of the invention where phase separation in lipid bilayers is analyzed.

A sensor according to the invention could be used to assess phase separation in bilayers using FRET. This is already done in flat substrates (Buboltz, J. T. Phys. Rev. E 2007, 76, 021903-1-7). Using it on nanowires and collecting all the light in one single plane would increase greatly its sensitivity and enable the detection of the formation of nano-domains earlier than when using flat substrates. The way to assess this is to label 2 different bilayer components (protein or lipid), known to have a propensity to segregate in two different phases (liquid ordered vs disordered) with a donor (for one bilayer component) and an acceptor (for the other bilayer component). The bilayer would be formed at a temperature above the phase separation temperature, at which the FRET signal should be maximum (since both donor and acceptor-labeled component are mixed). The temperature would be slowly decreased to monitor the formation of domains. Upon formation of domains, one should observe a decrease in the FRET signal and an increase of the donor fluorescence (FIG. 13).

Figure 9A:
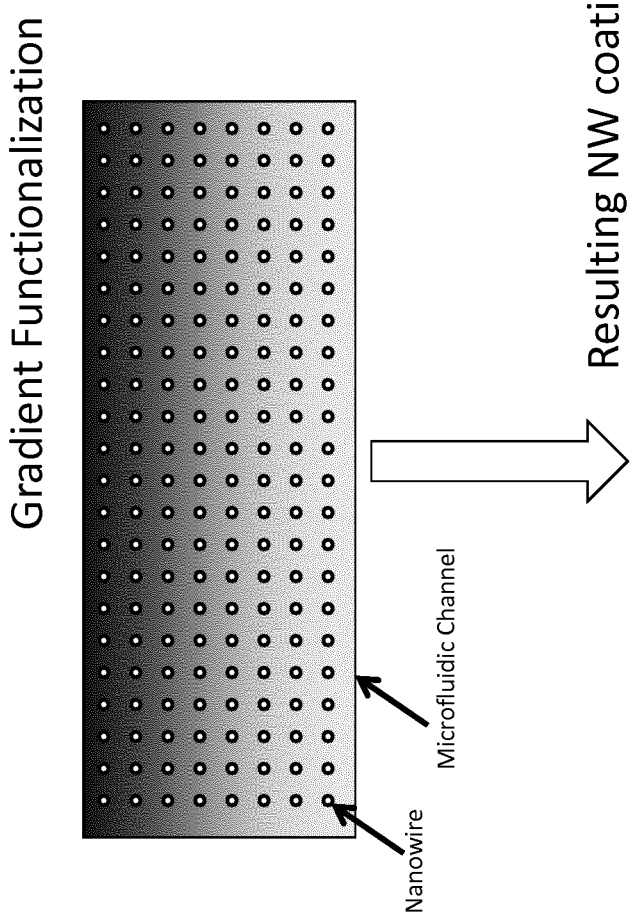
FIG. 9A shows a top view of an array of nanowires in a microfluidic channel with a gradient of functionalizing solute and the resulting nanowire array with coatings for a titration experiment.

A sensor according to the invention could be used in combination with microfluidics to increase spatial resolution due to the discrete point like emission achievable with the nanowires. In one embodiment, shown in FIG. 9A, an array of nanowires functionalized with a gradient of solute, e.g. using microfluidics. By using such an embodiment, a titration experiment could be done with one device with increased resolution of concentrations. Each nanowire tip in a row of the array, perpendicular to the concentration gradient, gives a number of point source readouts of the SALEPS adhered to the entire nanowire at different concentrations of initial functionalization. This will increase resolution from the now used microtiter plate well assays and decrease the amount of solution needed for a titration experiment. It gives an improved signal to a similar experiment without nanowires and the signal from the nanowires can be localized below typical resolution limits due to the discrete point like signal emitted from each nanowire. Uniform functionalization with a gradient of the binding molecules could also be done with the same benefits.

Figure 14:
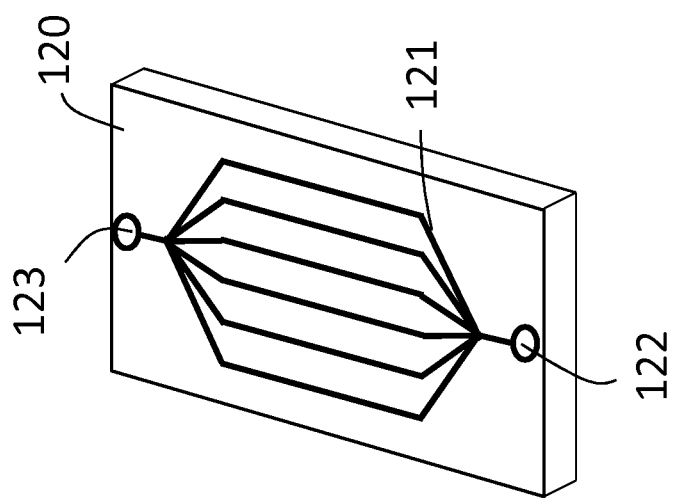
FIG. 14 schematically illustrates a microfluidic system comprising a nanowire molecular sensor.

In one embodiment, schematically illustrated in FIG. 14, an array of nanowires configured according to any of the embodiments described above may be integrated in a microfluidic system, which may be used to manipulate small miniscule vessels such as single cells. With current techniques it is difficult to detect antibodies secreted from single cells. This could be resolved in an embodiment of the invention, whereby the nanowire molecular sensor is incorporated into a microfluidic chamber. This would enable us to capture the antibodies in a small liquid volume, determined by the size of the microfluidics chamber, resulting in a high concentration of antibodies which would bind to the nanowires in the chamber for sensitive detection and direct readout. Such an embodiment is schematically illustrated in FIG. 14, in which a microfluidic chamber 120 is configured to carry the nanowires (not shown) in at least areas of microfluidic channels 121, extending from a first opening 122 to a second opening 123, through which a substance for analysis may flow. The microfluidic chamber 120 may be substantially transparent to light used to excite SALEPS and/or detect light fluorescent light from the nanowire ends. The substrates 31, carrying the nanowires 30, may for part of the chamber 120. Alternatively, the nanowires may be carried by a membrane-like substrate 31 placed in the channels 121. It is a well-known technology to transfer a grown array of nanowires from a semiconductor substrate to e.g. a polymer substrate, or to attach free nanowires to such a polymer substrate. Furthermore, it shall be noted that a chamber according to FIG. 14 may be used with an excitation device for illumination and a detection device for detecting light fluorescent light coupled to a nanowire waveguide and emitted through a nanowire end, at the same side of the chamber 120, or different sides, in accordance with the description provided with reference to FIGS. 11A-11D. In the shown example, a plurality of parallel channels 121 are shown, but other configurations are possible. In one embodiment, the different parallel channels may have different capabilities for attachment of molecules to the nanowires in the respective channel according to a gradient, with respect to functionalization or binding molecules as described with reference to FIG. 9A above.

In one embodiment, the nanowires are also configured to shape the angular distribution of emitted light, as taught in Nano Lett., 2015, 15 (7), pp 4557-4563. The nanowires can for example beam the emission from fluorophores bound to the surface of the nanowires into a narrow cone in the direction of the nanowire axis. This beaming occurs as follows: The emission from the fluorophores couples into a waveguide mode of the nanowires. The subsequent light in the waveguide mode propagates toward an end or tip of the nanowire. At the nanowire tip, the waveguide mode is coupled out from the nanowire, but with the modified angular radiation spectrum. This angular radiation spectrum can be tuned by the geometry of the nanowires, for example to beam light into a narrow, directed cone. In one embodiment of the invention, we do not spatially resolve the emission to distinguish light that originates from the tip of the nanowires. Instead, we use detection optics with a low numerical aperture (NA), which collects light emitted at an angle close to the direction of the nanowire axis. The benefit of this detection scheme is two-fold compared to a planar detector: First, we can use inexpensive low-NA detection of emission from large areas of nanowires. Second, the emission of unbound fluorophores are not coupled to the wave guide mode of the nanowires. Therefore, the emission of unbound fluorophores is not beamed in the axial direction of the nanowires. This difference in the angular distribution of the emission from unbound and bound fluorophores leads to an increased signal-to-noise ratio in the detection with the low-NA optics.

Because this device uses NF optical effects and the bulk solution fluorescence is low relative to that emitted at the tip of the nanowires, these devices could be used for kinetics studies of binding and unbinding target molecules. Without the need to remove the background signal from fluorescent molecules in bulk it is possible to use these devices to measure binding events in real time and use the increase or decrease in fluorescence form the nanowire tips over time to estimate binding on and off times of fluorescently labeled molecule in bulk that bind to the surface bound molecules.

The invention claimed is:

1. A waveguide molecular sensor comprising:
    a substrate;
    a nanowire comprising a semiconductor material and projecting from a front side of the substrate, the nanowire having two ends and a sidewall functionalized with a functionalizing element configured to attach specific molecules to the sidewall,
    wherein the nanowire is a waveguide configured to receive, through the sidewall, light having a wavelength of from 400 nm to 700 nm emitted from a light emissive point source that is attached to the specific molecules and that is positioned at a distance from the sidewall of less than half of the wavelength of the light, by using a near field coupling mechanism to directly couple the received light to a waveguiding mode in the nanowire, and to emit the received light from an end of the nanowire such that the emitted light can be detected in one focal point, and
    wherein the amount of light emitted from the end of the nanowire is dependent on the amount of the specific molecules attached to the sidewall.

2. The waveguide molecular sensor of claim 1, wherein said nanowire projects away from the front side of the substrate to a first nanowire end, and is attached to the substrate adjacent to a second nanowire end.

3. The waveguide molecular sensor of claim 1, wherein one end of the nanowire is optically connectable to an excitation device for injecting light into the nanowire, such that light is guided through the nanowire waveguide to excite the light emissive point sources.

4. The waveguide molecular sensor of claim 1, wherein the light emissive point sources comprise fluorophores.

5. The waveguide molecular sensor of claim 4, wherein the fluorophores are excited globally and the emitted light is detected in one focal point.

6. The waveguide molecular sensor of claim 5, wherein enhanced surface bound fluorescence is detected using a near field effect.

7. The waveguide molecular sensor of claim 6, wherein fluorescence from the environment is filtered out.

8. The waveguide molecular sensor of claim 1, wherein a plurality of nanowires with functionalized sidewalls are arranged mutually spaced apart to project substantially parallel to each other from said substrate, and wherein the light emitted from point sources at sidewalls of the nanowires can be detected in one focal plane.

9. The waveguide molecular sensor of claim 8, wherein the nanowires are provided in segments throughout the substrate surface, wherein the sidewalls of the nanowires of different segments are differently functionalized so as to attach different specific molecules.

10. The waveguide molecular sensor of claim 1, wherein the functionalizing element comprises proteins, receptors, molecules, a lipid bilayer, or a combination thereof.

11. A molecular detection system, comprising:
    the waveguide molecular sensor according to claim 1, wherein the front side of the substrate is configured to receive a substance such that the nanowire is exposed to the substance;

a light source positioned to emit light towards nanowire; and a photodetector positioned to detect light emitted from the end of the nanowire.

12. The molecular detection system of claim 11, wherein said photodetector has a focal plane, and is arranged with said focal plane substantially positioned to receive light emitted from the end of the nanowire.

13. The molecular detection system of claim 11, wherein the two ends of the nanowire comprise a first end distal from the substrate and a second end closer to the substrate than the first end.

14. The molecular detection system of claim 11, wherein the second end of the nanowire is positioned on the front side of the substrate and the detection device is positioned facing the first end of the nanowire and the front side of the substrate.

15. The molecular detection system of claim 11, wherein the detection device is positioned facing a rear side of the substrate opposite to the front side of the substrate and is configured to detect emitted light from the second end of the nanowire.

16. The waveguide molecular sensor of claim 1, further comprising a photodetector configured to detect light emitted from the nanowire.

17. The waveguide molecular sensor of claim 1, where the diameter of the nanowire contributes to a slow decay of the waveguiding mode.

18. The waveguide molecular sensor of claim 1, wherein the waveguiding mode is a HE11 waveguiding mode.

19. The waveguide molecular sensor of claim 1, wherein the diameter of the nanowire is 400 nm to 700 nm.

* * * * *